(12) United States Patent
Adams et al.

(10) Patent No.: US 7,524,459 B2
(45) Date of Patent: Apr. 28, 2009

(54) OPTOELECTRONIC AND MICROFLUIDIC INTEGRATION FOR MINIATURIZED SPECTROSCOPIC DEVICES

(75) Inventors: Mark L. Adams, Pasadena, CA (US); Stephen R. Quake, San Marino, CA (US); Axel Scherer, Laguna Beach, CA (US)

(73) Assignee: California Institute of Technology in Pasadena, Pasadena, CA (US)

( * ) Notice: Subject to any disclaimer, the term of this patent is extended or adjusted under 35 U.S.C. 154(b) by 524 days.

(21) Appl. No.: 10/351,294

(22) Filed: Jan. 23, 2003

(65) Prior Publication Data

US 2003/0235924 A1 Dec. 25, 2003

Related U.S. Application Data

(60) Provisional application No. 60/351,485, filed on Jan. 24, 2002.

(51) Int. Cl.
*B01L 3/00* (2006.01)
(52) U.S. Cl. ............. 422/82.05; 422/82.06; 422/82.09; 422/82.11; 422/100
(58) Field of Classification Search ............. 422/50, 422/68.1, 81, 82, 100, 82.05, 82.06, 82.08, 422/82.09, 82.11, 101, 102, 103, 104; 356/213, 356/244; 436/43, 52, 53, 63, 164
See application file for complete search history.

(56) References Cited

U.S. PATENT DOCUMENTS

| | | | |
|---|---|---|---|
| 5,235,412 A * | 8/1993 | Boisvert et al. ............. 348/659 |
| 5,650,123 A | 7/1997 | Saini et al. | |
| 5,653,939 A | 8/1997 | Hollis | |
| 5,965,410 A * | 10/1999 | Chow et al. ............. 435/91.2 |
| 6,054,277 A | 4/2000 | Furcht et al. | |
| 6,100,541 A | 8/2000 | Nagle et al. | |
| 6,136,212 A | 10/2000 | Mastrangelo et al. | |
| 6,197,503 B1 | 3/2001 | Vo-Dinh et al. | |
| 6,408,878 B2 * | 6/2002 | Unger et al. ............. 137/597 |
| 6,432,720 B2 * | 8/2002 | Chow ............. 436/180 |
| 6,899,137 B2 * | 5/2005 | Unger et al. ............. 137/833 |
| 6,929,030 B2 * | 8/2005 | Unger et al. ............. 137/883 |

OTHER PUBLICATIONS

Adams et al., "Microfluidic integration on detector arrays for absorption and fluorescence micro-spectrometers," *Sensors and Actuators A*, 3627:1-7 (2003).
Chou et al., "A microfabricated device for sizing and sorting DNA molecules," *PNAS*, 96:11-13 (1999).
Fu et al., "A microfabricated flourescene-activated cell sorter," *Nature Biotechnology*, 17:1109-1111 (1999).
Unger et al., "Monolithic Microfabricated Valves and Pumps by Multilayer Soft Lithography," *Science*, 288(5463):113-116 (2000).
Xia et al., "Soft Lithography," *Angew. Chem. Int. Ed.*, 37:550-575 (1998).
Xia et al., "Complex Optical Surfaces Formed by Replica Molding Against Elastomeric Masters," *Science*, 273:347-349 (1996).

* cited by examiner

*Primary Examiner*—Jill Warden
(74) *Attorney, Agent, or Firm*—Townsend and Townsend and Crew, LLP

(57) ABSTRACT

Techniques for integrating optoelectronic system and microfluidic system. An apparatus for optical analysis includes a detector system and a microfluidic system on the detector system. The apparatus is free from any lens system between the microfluidic system and the detector system. Methods of making such an apparatus and using such an apparatus are also disclosed.

13 Claims, 15 Drawing Sheets

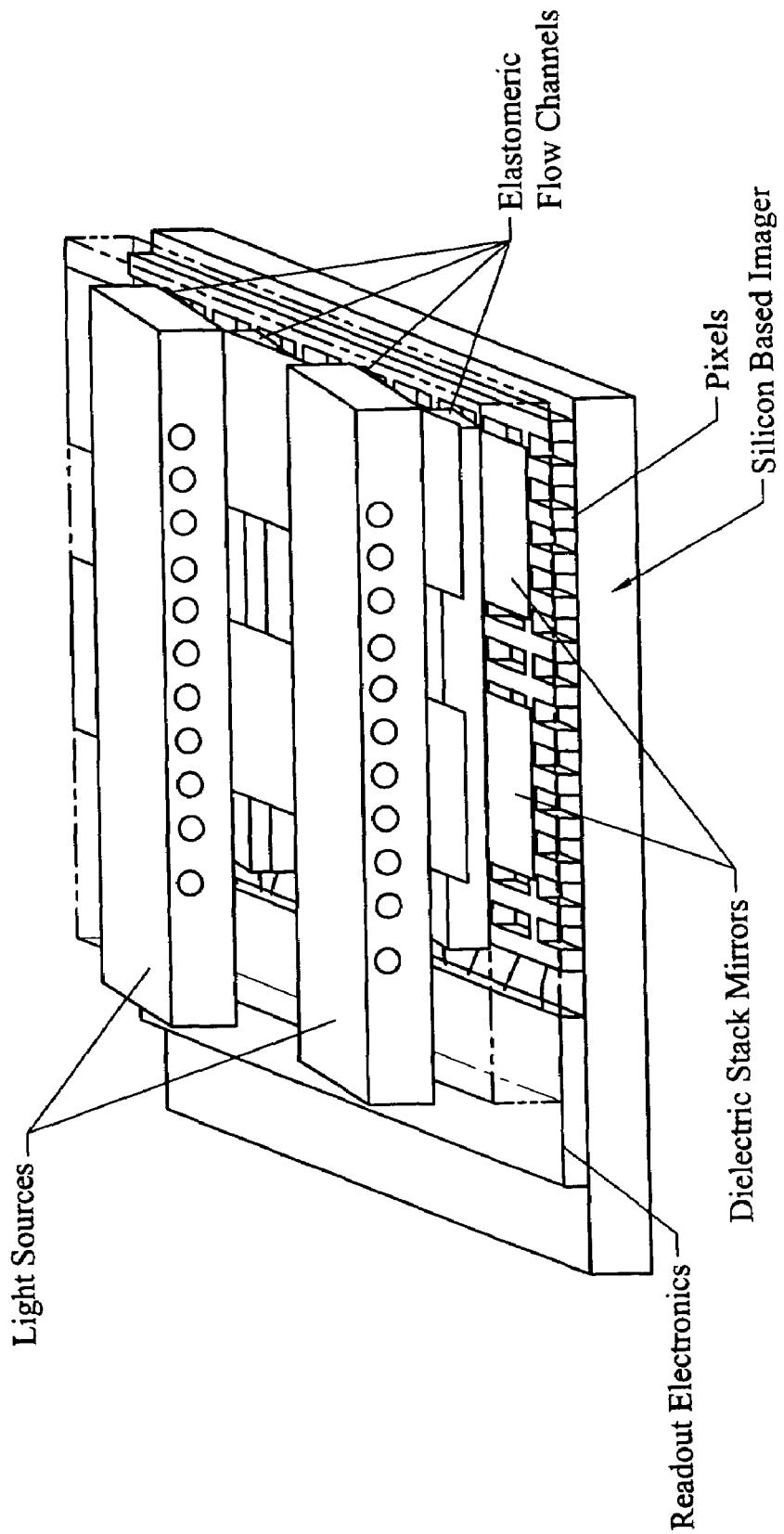

OPTOELECTRONIC AND MICROFLUIDIC INTEGRATION FOR MINIATURIZED SPECTROSCOPIC DEVICES

CROSS-REFERENCES TO RELATED APPLICATIONS

This application claims priority to U.S. Provisional No. 60/351,485 filed Jan. 24, 2002, which is incorporated by reference herein.

STATEMENT AS TO RIGHTS TO INVENTIONS MADE UNDER FEDERALLY SPONSORED RESEARCH OR DEVELOPMENT

Work described herein has been supported, in part, by NSF grant BES-0119493 and DARPA grant DAAD19-00-1-0392. The United States Government may therefore have certain rights in the invention.

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The present invention relates generally to optical analysis. More specifically, the invention provides a method and system for integrating optoelectronic systems and microfluidic systems. Merely by way of example, the invention has been applied to absorption spectroscopy and luminescence spectroscopy for microfluidic systems, but it would be recognized that the invention has a much broader range of applicability.

Microfluidic systems are usually analyzed with spectrometers. The effectiveness of spectrometers depends on structures of microfluidic systems. Microfluidic systems can be made of different materials, such as elastomer or semiconductor including silicon. These building materials affect the bandwidth available for spectroscopic analysis.

For example, microfluidic systems can be made of silicon. Silicon-based microfluidic structures usually suffer from the inability to perform optical analysis in the visible and near-ultraviolet spectral ranges. Due to the absorption edge of silicon, optical measurements in flow channels defined by silicon are usually limited to the infrared range and visible/ultraviolet spectroscopy is difficult to perform without using very elaborate geometries. For applications such as biochemistry, this difficulty poses a limitation since many absorption and fluorescence experiments are based on visible/UV fluorescent dyes.

In contrast, some elastomers are transparent in the visible and near ultraviolet spectral ranges. Hence elastomer-based microfluidic systems allow compact spectral analysis for chemical sensing and biological diagnostics. For example, fluorescently activated cell sorters based on pumps, valves and channels defined in RTV silicone elastomers have demonstrated excellent throughput and sorting accuracy. See A. Y. Fu, C. Spence, A. Scherer, F. H. Arnold, S. R. Quake, A microfabricated fluorescence-activated cell sorter, Nature Biotechnol. 17 (1999) 1109-1111. This article is hereby incorporated by reference for all purposes. These cell sorters have been fabricated inexpensively into very small and robust microfluidic devices. Chemical surface pretreatment of specific areas within a flow channel has led to the possibility of developing compact disease diagnostic chips, and even single molecule sizing systems can be built from elastomeric flow channels. In these applications, the overall size of the analysis system is typically limited by the dimensions of the optical excitation and detection components, and miniaturization of the readout optics is therefore desirable. However, miniaturization of grating-based spectrometer geometries is limited at least in part by a reduction of the spectral resolution, which can be predicted from the optical path lengths between the grating and the detection slit. For example, multi-wavelength 4 mm×12 mm spectrometers operating at 1500 nm typically yield a measured spectral resolution of approximately 1 nm. This compromise between resolution, insertion losses, and size usually limits the minimum size of such optical analysis systems.

Hence it is desirable to improve optical analysis techniques.

BRIEF SUMMARY OF THE INVENTION

The present invention relates generally to optical analysis. More specifically, the invention provides a method and system for integrating optoelectronic systems and microfluidic systems. Merely by way of example, the invention has been applied to absorption spectroscopy and luminescence spectroscopy for microfluidic systems, but it would be recognized that the invention has a much broader range of applicability.

According to an embodiment of the present invention, an apparatus for optical analysis includes a detector system and a microfluidic system on the detector system. The apparatus is free from any lens system between the microfluidic system and the detector system.

A method of making a system for optical analysis includes providing a detector system on a substrate system with connection to an electrical contact system. Additionally, the method includes providing a microfluidic system on the detector system by replication molding and providing a light source system coupled to the microfluidic system. The method is free from providing any lens system between the microfluidic system and the detector system.

According to yet another embodiment of the present invention, a method of using an apparatus for absorption spectroscopy includes loading test samples into a microfluidic system and placing the microfluidic system on a detector system. Additionally, the method includes providing a light source system coupled to the microfluidic system and sensing sample signals received at the detector system. Moreover, the method includes processing detector response signals and determining an absorption spectrum using at least information associated with detector response signals. The method is free from providing any lens system between the microfluidic system and the detector system.

According to yet another embodiment of the present invention, a method of using an apparatus for fluorescence spectroscopy includes loading test samples into a microfluidic system, placing the microfluidic system on a bottom filter system, and placing the bottom filter system on a detector system. Additionally, the method includes placing a light source system coupled to the microfluidic system and sensing sample signals received at the detector system. Moreover, the method includes processing detector response signals and determining an absorption spectrum using at least information associated with detector response signals. The method is free from providing any lens system between the microfluidic system and the detector system.

According to yet another embodiment of the present invention, an apparatus includes a light source configured to emit light of at least one wavelength, an photosensitive element including a pixel having a dimension, and a sample holding element located between the light source and the photosensitive element. The sample holding element comprises a material substantially transparent to light of the wavelength and includes a microfabricated recess configured to position a sample from the pixel at a distance of fifty-times the pixel dimension or less.

According to yet another embodiment of the present invention, a method includes providing a photosensitive element having a pixel having a dimension, and providing a light source configured to emit light of at least one wavelength. Additionally, the method includes disposing between the light source and the photosensitive element, a sample within a recess of a sample holding element, at a distance of fifty-times the pixel dimension or less. The sample holding element is substantially transparent to the light of the at least one wavelength. Moreover the method includes detecting with the photosensitive element an optical property of light from the sample.

Many benefits are achieved by way of the present invention over conventional techniques. For example, certain embodiments of the present invention can characterize spectra from picoliter volumes and observe a large number of flow channels simultaneously. Additionally, some embodiments of the present invention can use inexpensive and disposable fluidic components, and a very compact, robust and monolithic optical excitation and measurement system. Moreover, certain embodiments of the present invention can miniaturize spectroscopic instruments in microfluidic applications and provide "lens-less" images of contents in flow channels. Further, some embodiments of the present invention can be used with elastomer-based microfluidic system. Certain elastomer materials are inherently transparent in the visible spectral range and have similar UV absorption characteristics to those of glass. Also certain silicone elastomers can form a hermetic seal to the top surface of a filter system or a detector system.

Depending upon embodiment, one or more of these benefits may be achieved. These benefits and various additional objects, features and advantages of the present invention can be fully appreciated with reference to the detailed description and accompanying drawings that follow.

BRIEF DESCRIPTION OF THE DRAWINGS

FIG. 2A is a simplified diagram for an integrated spectroscopic system according to another embodiment of the present invention.

DETAILED DESCRIPTION OF THE INVENTION

The present invention relates generally to optical analysis. More specifically, the invention provides a method and system for integrating optoelectronic systems and microfluidic systems. Merely by way of example, the invention has been applied to absorption spectroscopy and luminescence spectroscopy for microfluidic systems, but it would be recognized that the invention has a much broader range of applicability.

Embodiments in accordance with the present invention provide approaches to reducing the size and complexity of optical systems. By positioning a sample in close proximity to an optical sensor, the embodiments of methods and apparatuses in accordance with the present invention may eliminate the need for focusing optics to be present between the sample and the detector. In accordance with one embodiment of the present invention, the sample may be positioned in close proximity (i.e. within a distance of 50× the dimension of the pixel of the detector) to the detector utilizing a microfabricated structure having a recess formed therein for receiving the sample. The microfabricated sample holding structure may be formed from any of a variety of materials substantially transparent to one or more the wavelengths of radiation of interest being applied to the sample, for example elastomer or quartz material.

Figure 1:
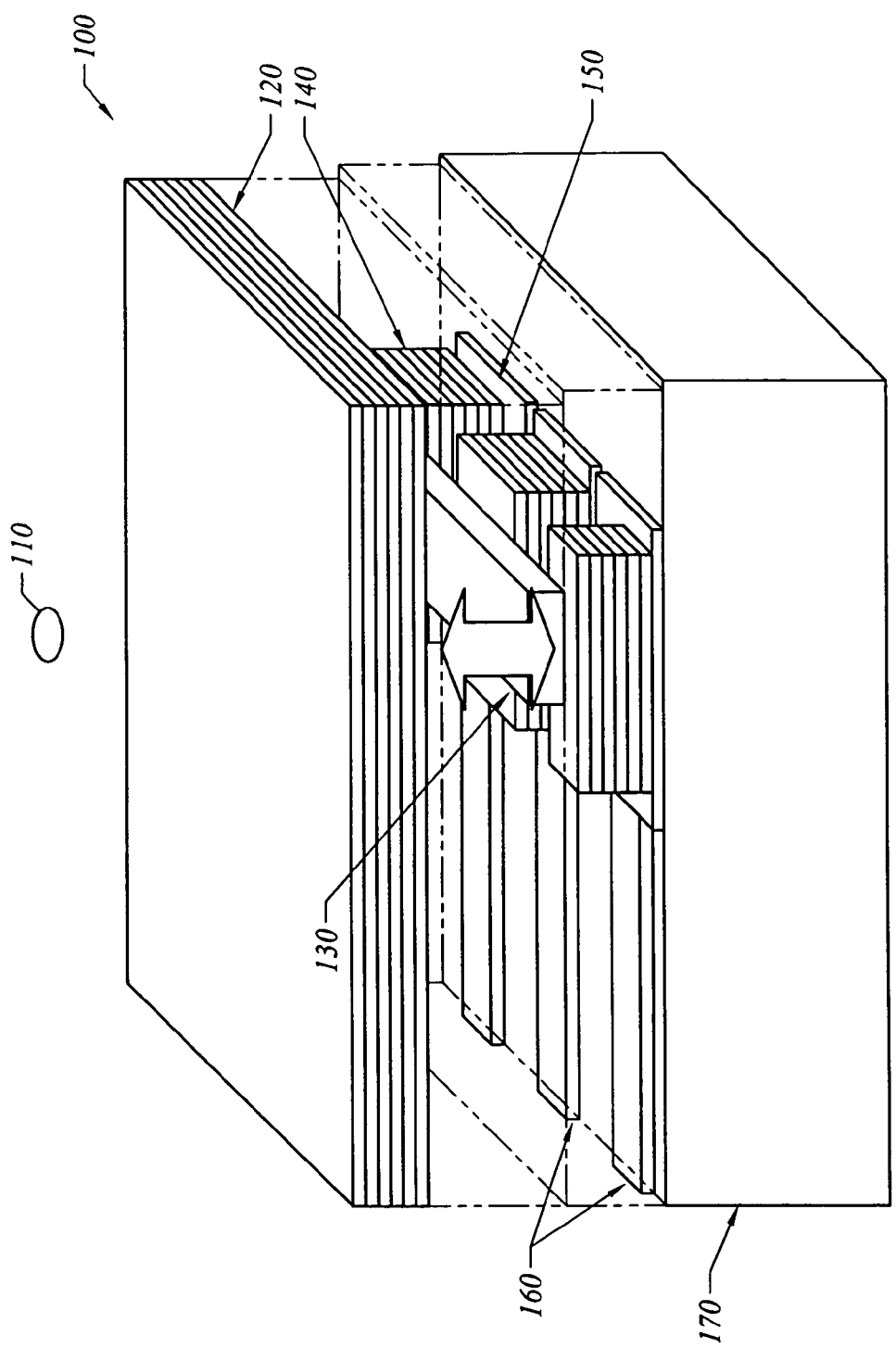
FIG. 1 is a simplified diagram for an integrated spectroscopic system according to one embodiment of the present invention.

FIG. 1 is a simplified diagram for an integrated spectroscopic system according to one embodiment of the present invention. This diagram is merely an example, which should not unduly limit the scope of the claims. One of ordinary skill in the art would recognize many variations, alternatives, and modifications. Integrated spectroscopic system 100 includes light source system 110, top filter system 120, microfluidic system 130, bottom filter system 140, and detector system 150. Although the above has been shown using selected systems 110 through 150, there can be many alternatives, modifications, and variations. For example, some of the systems can be expanded and/or combined. Light source system 110 and top filter system 120 may be combined. Bottom filter system 140 and detector system 150 may be combined. Top filter system 120, microfluidic system 130, and bottom filter system 140 may be combined. Other systems may be added to those noted above. Electrical contact system 160 may be added to read out signals generated by detector system 150. Substrate system 170 may be added to support detector system 150. Depending upon the embodiment, some of the systems may be removed. Top filter system 120, bottom filter system 140, or both filter systems 120 and 140 may be removed.

In FIG. 1, light source system 110 provides illumination for spectroscopic analysis performed by integrated spectroscopic system 100. The illumination usually has a bandwidth covering infrared ("IR") spectral range, visible spectral range, ultraviolet ("UV") spectral range, or any combination thereof. For example, light source system 110 can provide visible and UV illumination to microfluidic system 130. Light source system 110 has one or several light sources, as shown in FIGS. 1 and 2A. Multiple light sources can be used to uniformly illuminate sample areas subject to spectroscopic analysis. Additionally, light source 110 may provide a collimated beam or a non-collimated beam. The collimated beam usually improves the spatial resolution of detector system 150.

According to one embodiment of the present invention, light source system 110 has a tungsten or tungsten-iodine filament lamp which may also include light emitting diodes. In a miniature spectrometer, the appropriate light source depends heavily upon the application and heat dissipation problems. Some convenient alternatives include solid-state light emitting diodes, laser light sources such as laser diodes, white light sources, and even the Sun. For infrared analysis, the source might also be a tungsten filament lamp with a specific color filter placed directly over microfluidic system 130. For many applications of the present invention, an array of vertical cavity surface emitting lasers ("VCSELs") could be desirable. Alternatively, high finesse optical cavity filters can be defined on top of light emitting diode arrays to obtain filtered light sources, which can be directly placed on top of microfluidic channels, which in turn are placed on top of detector system 150, to create a fully functional on-chip spectrometer.

Figure 2B:
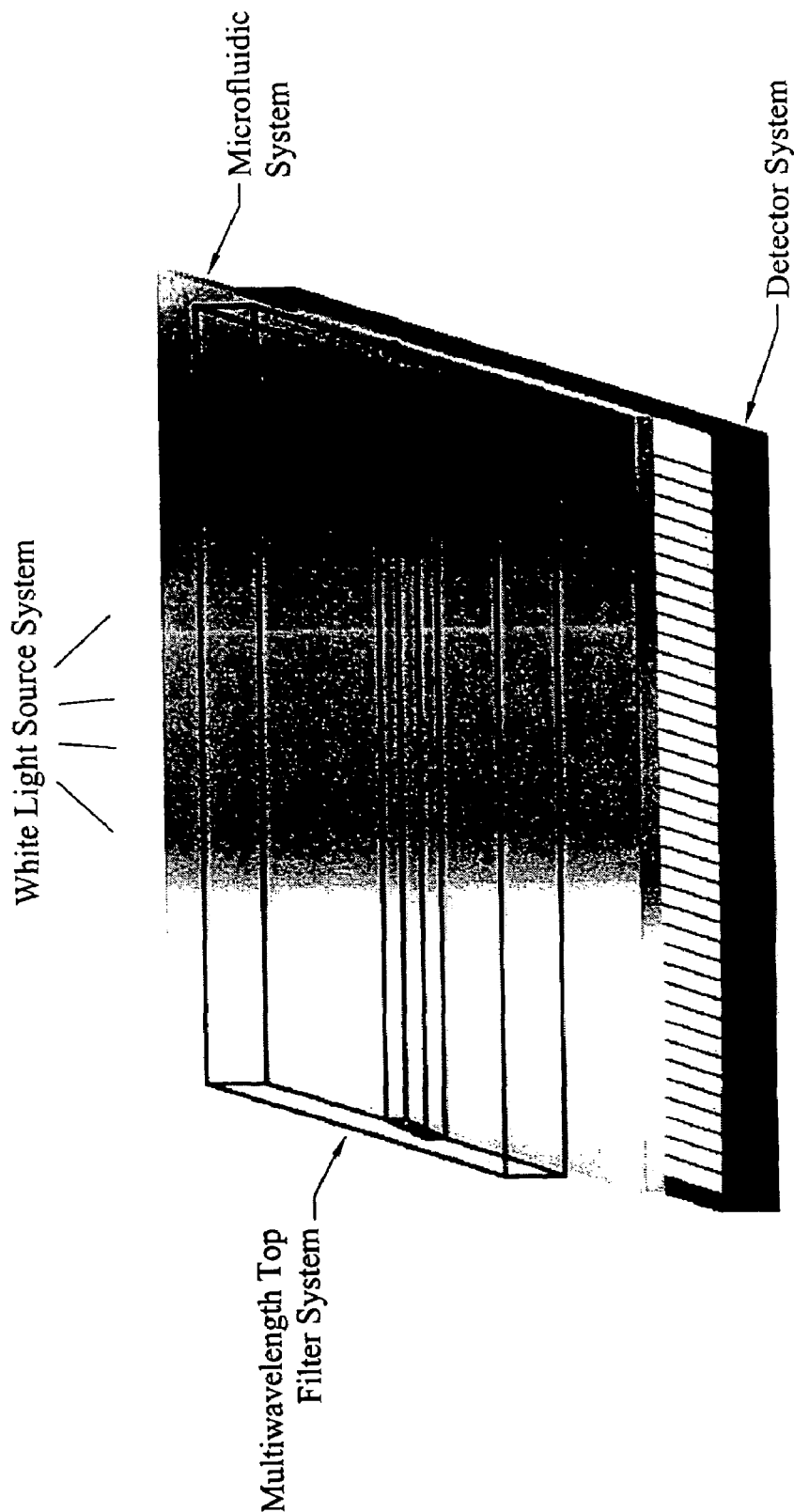
FIG. 2B shows a simplified multiwavelength filter system according to an embodiment of the present invention.

Top filter system 120 blocks illumination at certain wavelengths from light source system 110. For example, top filter system 120 provides strong reflection or absorption at given wavelengths and thereby significantly reduces light intensity received by microfluidic system 130. Additionally, top filter system 120 can enhance light intensity passing through microfluidic system 130 at certain wavelengths. For example, top filter system 120 can provide strong reflection to light beams at certain wavelengths that have passed through microfluidic system 130 and been reflected off any reflection layer under microfluidic system 130. The reflection layer may be bottom filter system 140. As another example, FIG. 2A shows that top filter system 120 includes a stack mirror. The stack mirror can be made of dielectric materials such as $SiO_2$, $Si_3N_4$, or other material such as silicon. The stack mirror may include at least two layers with different indexes of refraction. In some embodiments of the present invention, the $Si_3N_4$ layers and the $SiO_2$ layers can be made with a deliberate thickness variation across the top surface of microfluidic system 130 and thereby forms a multiwavelength filter system. FIG. 2B shows a simplified multiwavelength filter system according to an embodiment of the present invention. In FIG. 2B, top filter system 120 selectively transmits light illumination of different wavelengths at different locations and create spectral variations across the top surface of microfluidic system 130. Depending on embodiments, top filter system 120 may be optional. In some examples, top filter system 120 performs both band blocking function and cavity enhancement function. In other examples, top filter system 120 performs only band blocking function or cavity enhancement function.

Microfluidic system 130 contains test samples subject to spectroscopic analysis. Microfluidic system 130 is made of elastomer, glass, quartz, semiconductor including silicon, or other material. Silicon is substantially opaque in visible and UV ranges, so a silicon-based microfluidic system is usually applicable only to infrared spectroscopy according to one embodiment of the present invention. In contrast, elastomer can be transparent in at least a portion of IR, visible and UV spectral ranges; hence an elastomer-based microfluidic system can be analyzed in a wide bandwidth. The specific types of elastomers used include at least PDMS, polyurethane, polyimide, and parylene. PDMS has mechanical flexibility that is highly desirable for microfluidic system 130, and polyurethane provides good biocompatibility and mechanical flexibility. Alternatively, microfluidic system 130 can be made of quartz. Quartz is usually transparent even in short UV spectral range; hence a quartz-based microfluidic system can provide a broad bandwidth for spectroscopic analysis according to yet another embodiment of the present invention.

Figure 2C:
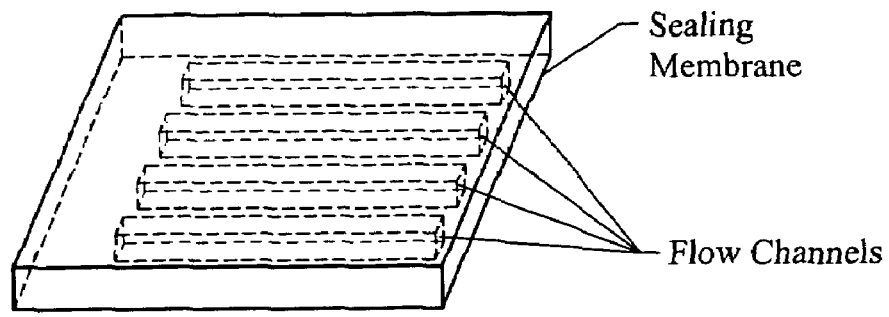
FIG. 2C shows a simplified microfluidic system with flow channels encapsulated by sealing membranes according to an embodiment of the present invention.

For example, FIG. 2A shows a simplified microfluidic system 130 having flow channels. The flow channels contain test samples subject to optical analysis. The flow channels can be made of elastomer, glass, quartz, semiconductor including silicon, or other material. According to one embodiment of the present invention, elastomer channels are placed directly on top of bottom filter system 140 or detector system 150. Alternatively, FIG. 2C shows elastomer flow channels encapsulated by sealing membranes. The sealing membranes protect bottom filter system 140 and detector system 150 from contamination by contents within flow channels. Therefore, integrated spectroscopic system 100 may be reused for many microfluidic systems. Through sealing membranes, inlets and outlets exist for flow channels. The inlets and outlets may be on one or several sealing membranes, such as a top membrane, a bottom membrane, or a side membrane.

Bottom filter system 140 can block illumination at certain wavelengths from reaching detector system 150. For example, bottom filter system 140 provides strong reflection or absorption at given wavelengths and thereby significantly reduces light intensity received by detector system 150. Additionally, bottom filter system 140 can enhance light intensity passing through microfluidic system 130 at certain wavelengths. For example, bottom filter system 140 can provide strong reflection to light signals that have passed through microfluidic system 130. FIG. 2A shows a bottom filter system 140 having a dielectric stack mirror. The stack mirror may include at least two layers with different indexes of refraction. In some embodiments of the present invention, bottom filter system 140 is optional. In other embodiments of the present invention, bottom filter system 140 performs both band blocking function and cavity enhancement function as discussed above. In yet other embodiment of the present invention, bottom filter system 140 performs only either band blocking function or cavity enhancement function.

Figure 2D:
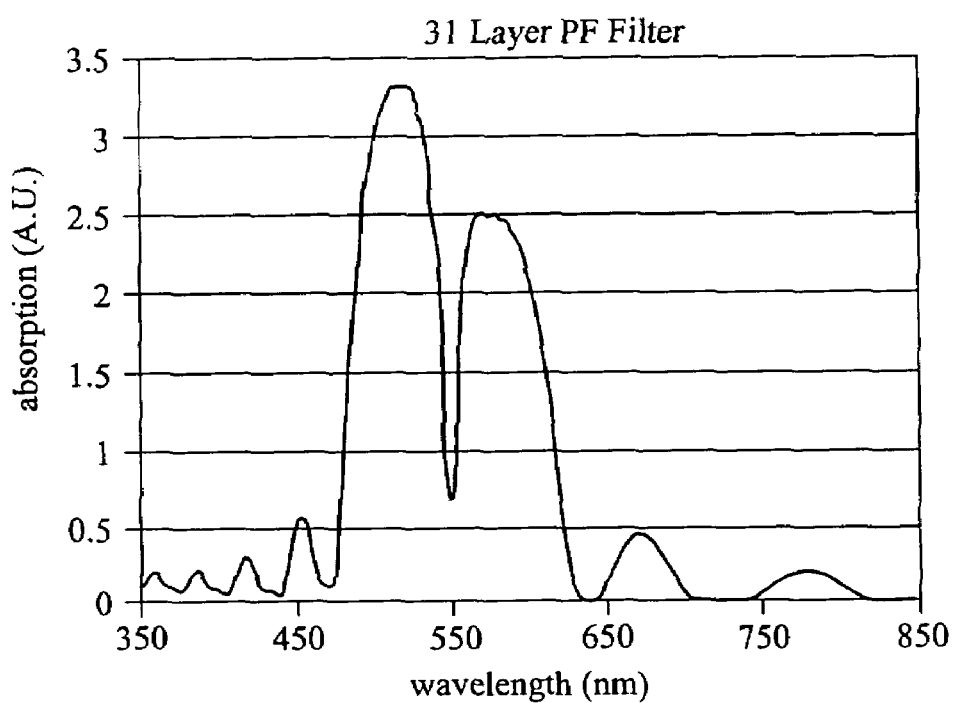
FIG. 2D is a simplified absorption spectra of a filter system.

FIG. 2D is a simplified absorption spectra for bottom filter system 140. This diagram is merely an example, which should not unduly limit the scope of the claims. One of ordinary skill in the art would recognize many variations, alternatives, and modifications.

Figure 2E:
FIG. 2E show spectral variation across a filter system according to an embodiment of the present invention.

Bottom filter system 140 have $Si_3N_4/SiO_2$ multilayer Fabry-Perot cavities. The $Si_3N_4$ layers are deposited onto respective $SiO_2$ layers. The $Si_3N_4$ layers and the $SiO_2$ layers can be made with a deliberate thickness variation across the imaging surface of detector system 150 and therefore create spectral variation as shown in FIG. 2E. Consequently, detector system 150 can obtain a specific wavelength response for each pixel in the imaging array. By pumping the solution of interest over these filtered pixels and observing their response, a spectrum of the absorption or luminescence of a small solution volume can be obtained.

Detector system 150 detects light signals passing through microfluidic system 130. Detector system 150 can have stronger sensitivity at certain wavelengths than other wavelengths. For example, detector system 150 may be tailored to detect signals in IR spectral range, visible spectral range, UV spectral range, or any combination thereof. Detector system 150 may comprise silicon-based avalanche photodiodes, charge coupled devices, CMOS integrated p-n diode sensors ("CMOS imagers"), or other detectors. All of these devices are commercially available at reasonable costs. The charge coupled devices usually have small pixels and are generally sensitive to light signals, but they usually require readout of the entire image information in order to determine intensity information from pixels directly underneath test samples of microfluidic system 130. The avalanche photodiodes usually require larger detection areas and therefore may have only limited imaging resolution. The CMOS imagers offer direct addressing of individual pixels and change of individual pixel integration times, and therefore can provide faster response times and long integration times. As shown in FIG. 2A, detector system 150 may include silicon-based imagers with multiple pixels.

According to one embodiment of the present invention, the highest resolution of detector system 150 is determined by the pixel size on the imaging array and can be less than 10 µm. For example, pixel size may be 8 µm×8 µm, 9 µm×9 µm, 10 µm×10 µm, or other. The sensitivity of the imaging system is in turn dependent on the active area of the pixel, as well as leakage currents in the pixels. For example, the active area of the pixel may be 3 µm×3 µm or others. Other factors determining the performance of an imaging detector array in a spectrometer application are sensitivity and dynamic range. Sensitivity becomes extremely important when examining picoliter volumes with a correspondingly small optical interaction length.

The present invention does not require focusing optics between microfluidic system 130 and detector system 150. For example, the present invention places microfluidic system 130 directly onto detector system 150 with only bottom filter system 140 in between or without any intermediate layer. Microfluidic system 130 is in close proximity to detector system 150.

Detector system 150 may be electrically connected to electrical contact system 160, as shown in FIG. 1. For example, electrical contact system 160 includes readout electronics as shown in FIG. 2A. The readout electronics acquires response signals from detector system 150 and sends such signals for further signal processing. In certain embodiments, detector system 150 may be placed on substrate system 170, as shown in FIG. 1. The substrate system 170 can include a silicon substrate. Substrate system 170 can include signal processing circuitry to analyze response signals transmitted from electrical contact system 160.

Figure 3:
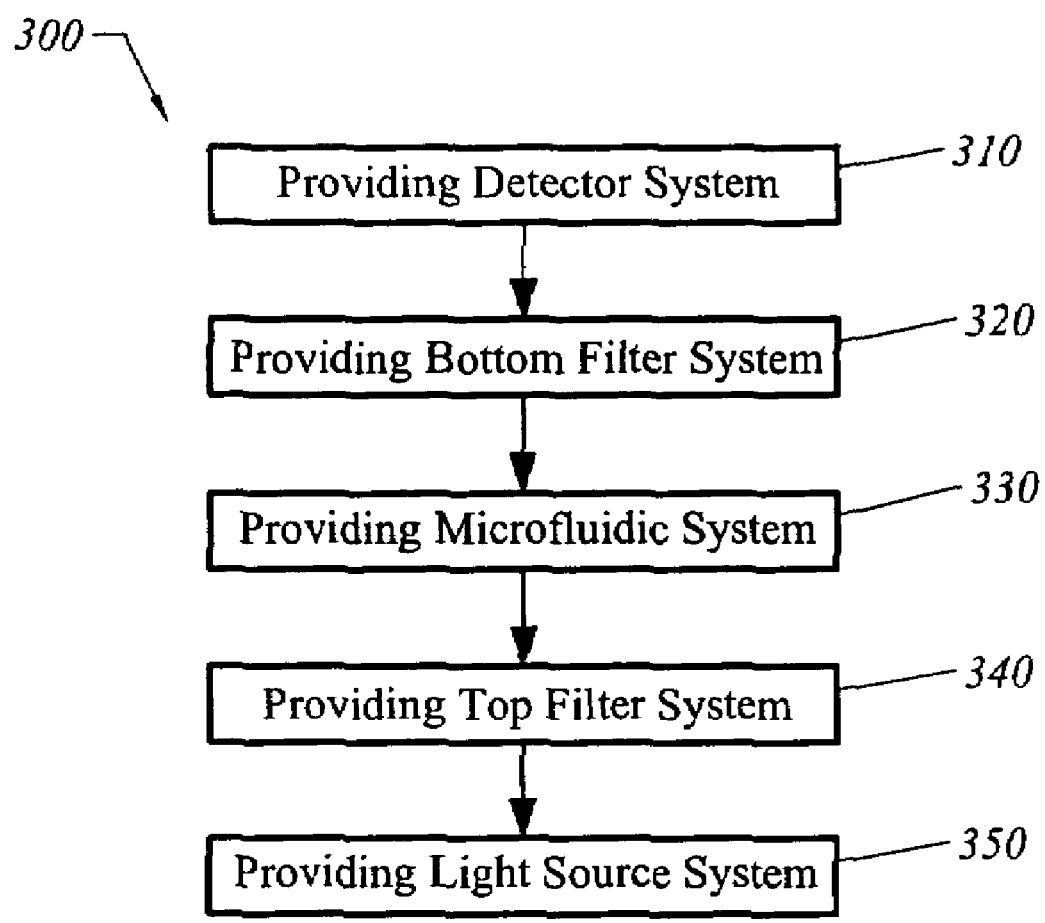
FIG. 3 is a simplified block diagram for a method of making an integrated spectroscopic system according to one embodiment of the present invention.

FIG. 3 is a simplified block diagram for a method of making an integrated spectroscopic system according to one embodiment of the present invention. This diagram is merely an example, which should not unduly limit the scope of the claims. One of ordinary skill in the art would recognize many variations, alternatives, and modifications.

The method 300 of making an integrated spectroscopic system includes process 310 for providing detector system, process 320 for providing bottom filter system, process 330 for providing microfluidic system 330, process 340 for providing top filter system, process 350 for providing light source system, and possibly others, depending upon the embodiment. Although the above has been shown using a selected sequence of processes, there can be many alternatives, modifications, and variations. For example, some of the processes may be expanded and/or combined. Process 310 for providing detector system and process 320 for providing bottom filter system may be combined. Process 340 for providing top filter system and process 350 for providing light source system may be combined. Depending upon the embodiment, the specific sequence of processes may be interchanged with others replaced. For example, process 320 for providing bottom filter system may be skipped. Similarly, process 340 for providing top filter system may be skipped. Also, both processes 320 and 330 may be skipped. Moreover, sequences of processes 310 through 350 may be changed in various ways. For example, these processes may be performed starting from process 350 through process 310 in reverse order. Alternatively, processes 310 and 320 and processes 340 and 350 may be performed prior to process 330. Also alternatively, processes 320, 330, and 340 may be performed to sandwich a microfluidic system between a bottom filter system and a top filter system prior to processes 310 and 350. Further details of these processes are found throughout the present specification and more particularly below.

Figure 4:
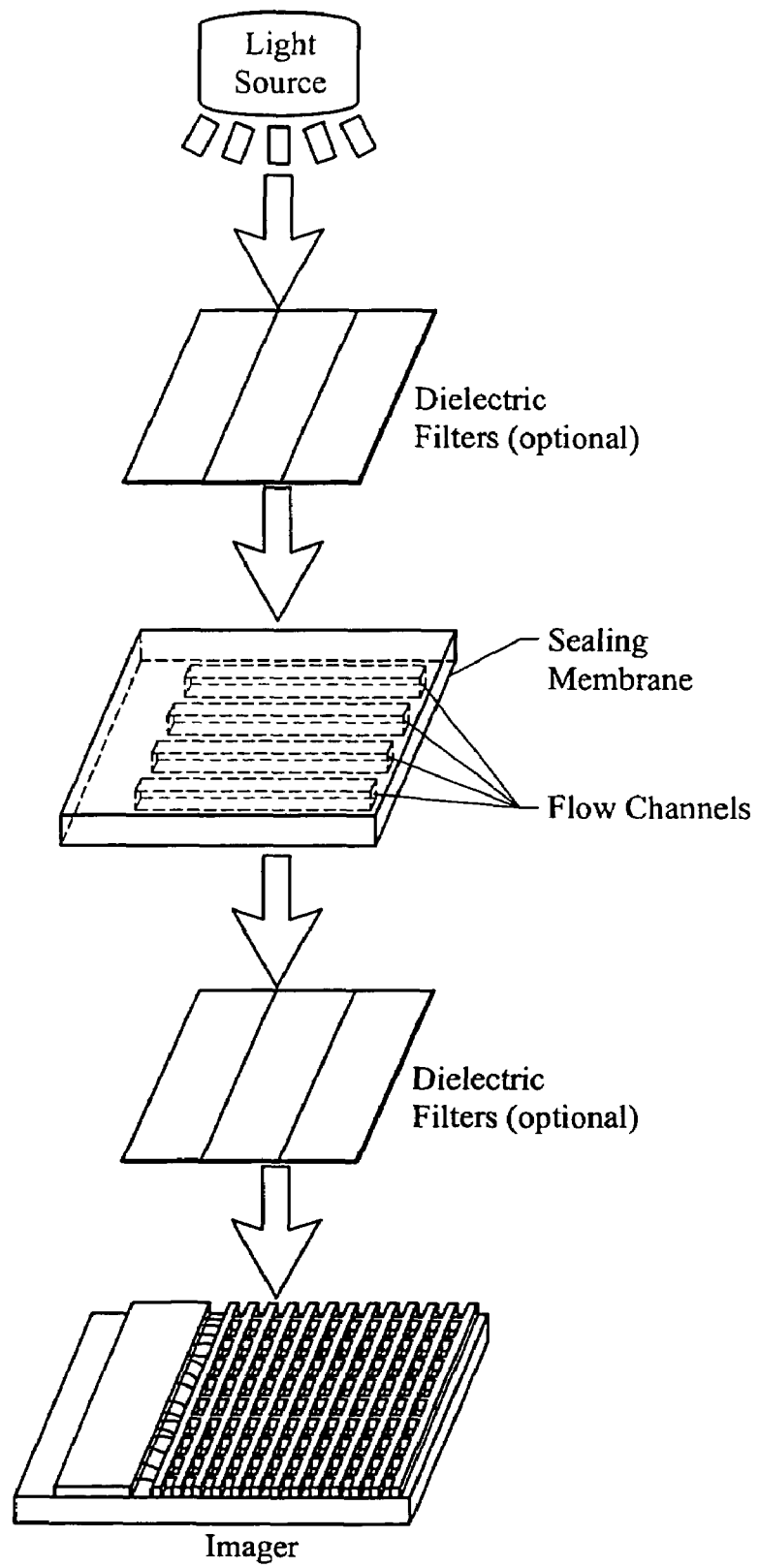
FIG. 4 is a simplified diagram for a method of making an integrated spectroscopic system according to another embodiment of the present invention.

FIG. 4 is a simplified diagram for a method of making an integrated spectroscopic system according to another embodiment of the present invention. This diagram is merely an example, which should not unduly limit the scope of the claims. One of ordinary skill in the art would recognize many variations, alternatives, and modifications.

At process 310 for providing detector system, detector system 150 is selected and installed. For example, detector system 150 may be placed on top of substrate system 170 with connection to electrical contact system 160. Detector system 150 may be integrated with substrate system 170, and the integration process may utilize various semiconductor process techniques, such as lithography, deposition, etching, and ion implantation.

At process 320 for providing bottom filter system, bottom filter system 140 is placed on detector system 150. For example, as shown in FIG. 4, bottom filter system 140 includes a dielectric filter. The dielectric filter may include layers of silicon nitride and silicon oxide. These layers may be formed by various techniques, including but not limited to RF plasma sputtering deposition. The plasma sputtering deposition may use a silicon sputtering target, oxygen gas and nitrogen gas, and can produce high quality films with low stress. For certain embodiments of the present invention, process 320 can be skipped.

At process 330 for providing microfluidic system, microfluidic system 130 is placed on detector system 150 with or without bottom filter system 140 in between. According to one embodiment of the present invention, microfluidic system 130 may be fabricated by replication molding of elastomer. Replication molding involves curing an elastomer, typically silicone based, on a microscopic mold. The mold can be generated through bulk or surface micromachining, but is usually generated via photolithography. One method for creating a mold suitable for a microfluidic system includes exposing thick UV sensitive photoresist using high-resolution contact photolithography. The resulting mold pattern is then developed and treated with a delamination agent to prevent adhesion between the mold and the cured elastomer. The elastomer can be cast on top of the mold by either pouring a thick layer, or spinning a thin layer onto the patterned surface. See M. A. Unger, H. Chou, T. Thorsen, A. Scherer, S. Quake, Monolithic Microfabricated Valves and Pumps by Multilayer Soft Lithography, Science 288 (2000) 113-116. This reference is hereby incorporated by reference for all purposes.

For example, as shown in FIG. 4, microfluidic system 130 includes flow channels placed in sealing membranes. In some embodiments, both flow channels and sealing membranes are made of PDMS. Nonetheless PDMS for flow channels and PDMS for sealing membranes may have different PDMS ratios. These PDMS materials form a strong interface after curing. With sealing membranes, microfluidic system 130 may be simply placed onto bottom filter system 140 or detector system 150 and form a strong interface. The interface may withstand a force equal to about 3 psi. Alternatively, the flow channels are directly placed onto bottom filter system 140 or detector system 150 without any sealing membrane. The process, for example, includes baking the flow channels and bottom filter system 140 or detector system 150 at 90° C. for a couple of hours and forms an interface that can withstand a force equal to about 30 psi.

As discussed above, using the replication molding technique, many microfluidic devices such as peristaltic pumps, pneumatic valves, circular mixers, and fluorescently activated cell sorters can be made. See H. Chou, C. Spence, A. Scherer, S. Quake, A microfabricated device for sizing and sorting DNA molecules, Proc. Natl. Acad. Sci. USA 96 (1999) 11-13. This reference is hereby incorporated by reference for all purposes. To define simple pneumatic valves with picoliter dead volumes, the multilayer replication technique is used, in which a pneumatic layer is aligned onto the fluidic layer. The elastomer between the two layers can be thinner than 10 µm, and can be deflected with low pressures introduced from the pneumatic control source. One or more of these valves can be integrated to define a peristaltic pump, to move solution over detector system 150, which can provide spectroscopic information about the analyte flowing in flow channels. Furthermore, valves and pumps can be combined to define fluidic cell sorters with feedback in which the cell examination time can be dynamically controlled during the sorting process. Since the silicone elastomer usually is natively hydrophobic, the sample can be placed in 0.001 MHCl solution at 80° C. for several minutes to make it hydrophilic, if the natural hydrophobic state is an issue.

At process 340 for providing top filter system, top filter system 120 is placed on microfluidic system 130. For example, as shown in FIG. 4, top filter system 120 includes a dielectric filter. According to one embodiment of the present invention, the dielectric layer includes layers of silicon nitride and silicon oxide. These layers may be formed by various techniques, such as lithography, deposition, etching, and ion implantation. For example, the dielectric filter is formed by room temperature plasma sputtering deposition using a silicon sputtering target, oxygen gas and nitrogen gas. For certain embodiments of the present invention, process 340 is skipped.

At process 350 for providing light source system, light source system 110 is placed above microfluidic system 130. Between microfluidic system 130 and light source system 110, there may be optionally top filter system 120. According to one embodiment of the present invention, light source system 110 makes direct contact with at least one of microfluidic system 130 and top filter system 120. Alternatively, light source system 110 is placed without making direct contact with either microfluidic system 130 or top filter system 120 as shown in FIG. 4.

Figure 5A:
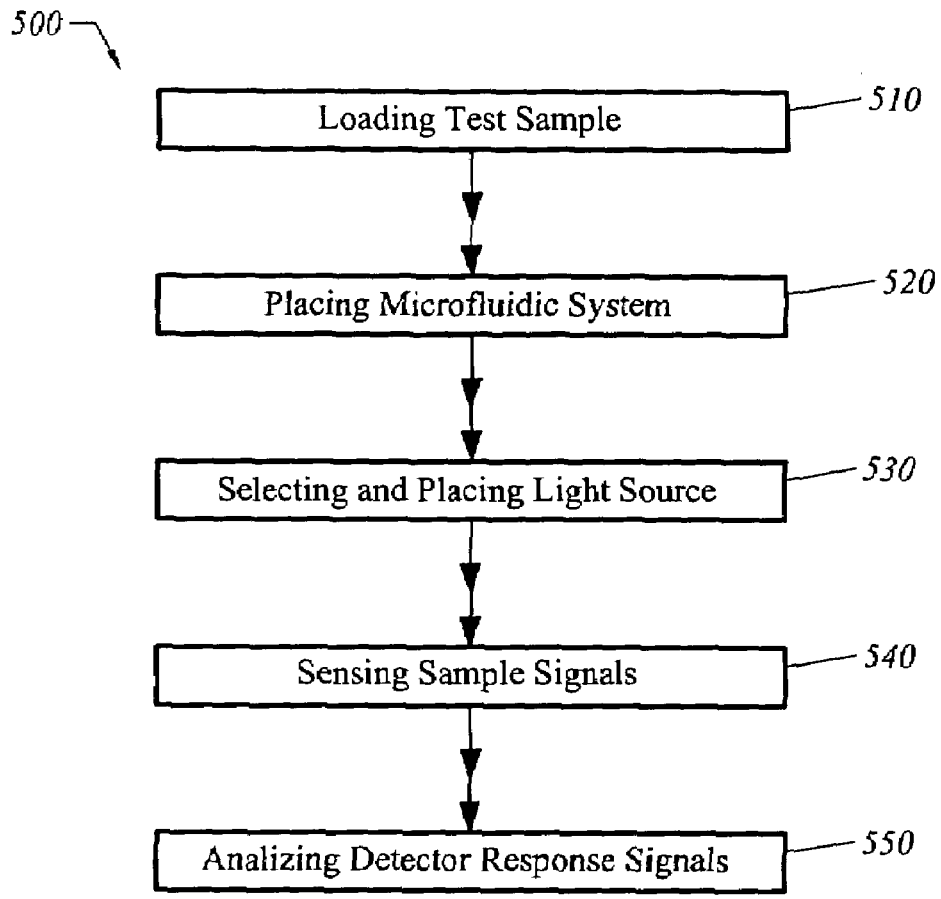
FIG. 5A is a simplified diagram for a method of using an integrated spectroscopic system for absorption spectroscopy according to one embodiment of the present invention.

FIG. 5A is a simplified diagram for a method of using an integrated spectroscopic system for absorption spectroscopy according to one embodiment of the present invention. This diagram is merely an example, which should not unduly limit the scope of the claims. One of ordinary skill in the art would recognize many variations, alternatives, and modifications. The method 500 of using an integrated spectroscopic system for absorption spectroscopy includes process 510 of loading a test sample into microfluidic system, processes 520 of placing the microfluidic system on a detector system or a bottom filter system, process 530 of selecting and placing a light source system, process 540 of sensing sample signals received at the detector system, process 550 of analyzing detector response signals, and possibly others, depending upon the embodiment.

Figure 5B:
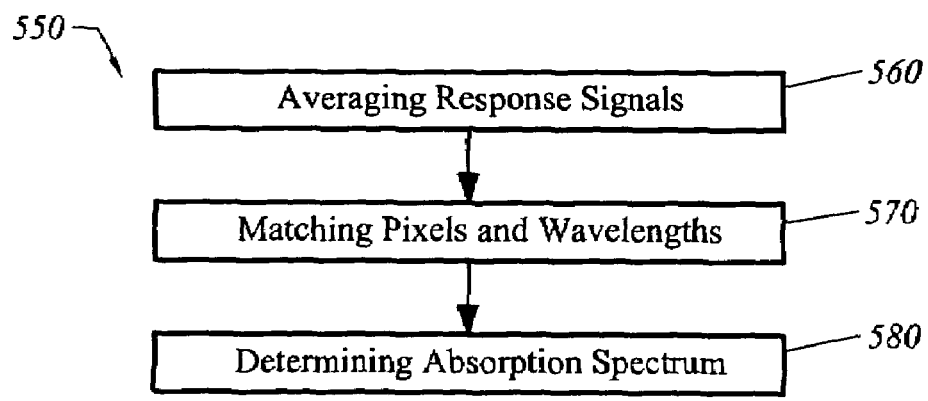
FIG. 5B is a simplified diagram for analyzing detector response signals according to one embodiment of the present invention.

Although the above has been shown using a selected sequence of processes, there can be many alternatives, modifications, and variations. For example, some of the processes may be expanded and/or combined. Process 530 of selecting and placing a light source system may include selecting and placing a top filter system. Process 550 of analyzing detector response signals may include process 560 of averaging response signals from pixels whose input sample signals have substantially the same wavelength, process 570 of matching individual pixels and wavelengths of their input sample signals, and process 580 of determining sample absorption spectrum, as shown in FIG. 5B. Depending upon the embodiment, the specific sequence of processes may be interchanged with others replaced. Processes 510 through 550 may be modified to acquire response signals resulting from a broadband of sample signals by using a wideband light source system and removing top filter system and bottom filter system. Further details of these processes are found throughout the present specification and more particularly below.

Figure 6:
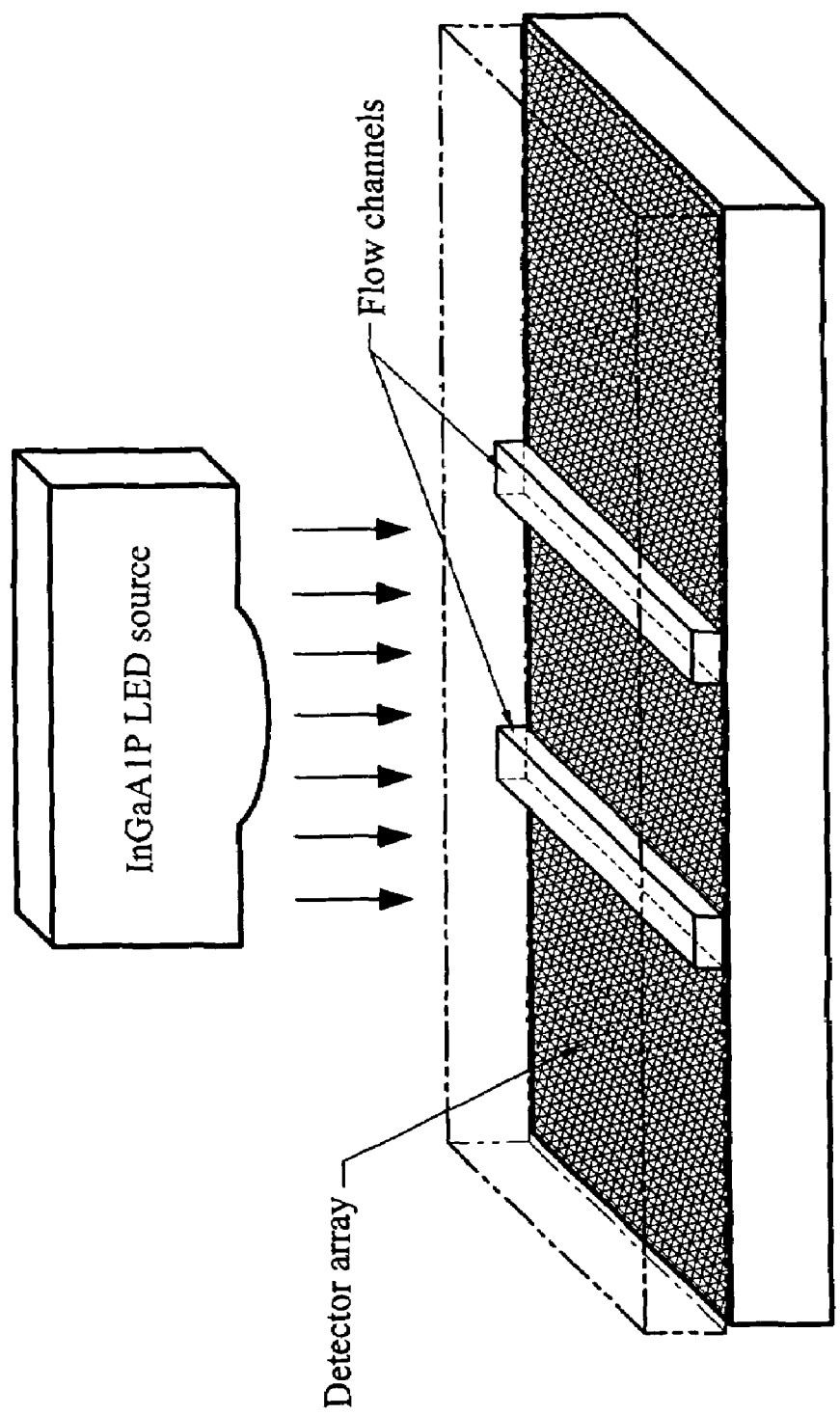
FIG. 6 is a simplified diagram for a method of using an integrated spectroscopic system for absorption spectroscopy according to another embodiment of the present invention.

FIG. 6 is a simplified diagram for a method of using an integrated spectroscopic system for absorption spectroscopy according to another embodiment of the present invention. This diagram is merely an example, which should not unduly limit the scope of the claims. One of ordinary skill in the art would recognize many variations, alternatives, and modifications. In FIG. 6, the light source system includes a 588 nm AlInGaP light emitting diode placed above flow channels of the microfluidic system. The detector system includes a CMOS camera chip having a detector array.

For absorption spectroscopy, the absorbance is proportional to the concentration of the absorbing material and the absorption path length as shown below.

$$A = \epsilon \times c \times l, \text{ where:} \quad \text{(Equation 1)}$$

A=absorbance
$\epsilon$=molar absorption constant or molar absorptivity
c=concentration of the absorbing material
l=absorption path length In some embodiments of the present invention, the size of an elastomer microfluidic channel is on the order of 50-250 µm wide by 10-20 µm deep, so the absorption path length l is small. Therefore, the difference in the expected detected intensity of a channel filled with reagent versus a channel filled with water may be small for dilute solutions. Consequently, the higher the sensitivity of the detectors in the sensor array, the greater the concentration range that can be detected.

Additionally, equation 1 shows that the absorbance improves with the absorption path length. The absorption path length can be increased by designing a vertical cavity structure, by for example placing a thin-film, λ/4 dielectric stack mirror tuned to the appropriate wavelength on top of the detector system and also on top of the microfluidic system. The cavity is formed between the two mirrors and allows for multiple passes of the pump light through the solution under test.

EXAMPLE OF ABSORPTION EXPERIMENT

An absorption experiment was performed using a 10-bit resolution black and white CMOS imager provided by NASA's Jet Propulsion Laboratory. This imager has a typical pixel size of 12 μm, a dynamic range larger than 65 dB, and a responsivity larger than 1.3 mV/photon at room temperature. The active imaging area had 512×512 pixels. First, the minimum concentration of dye that can be detected in the integrated spectroscopic system was determined. The absorptivity of various concentrations of bromophenol blue on a calibrated spectrometer was tested with solution filled into 1 cm cuvettes. For example, bromophenol blue is Aldrich Chemical Company, Inc., #62625-28-9, and the calibrated spectrometer is Shimadzu BioSpec 1601 spectrophotometer. The molar absorption constant was then calculated and a curve fit was applied to generate the control data for a 14 μm channel.

Figure 7:
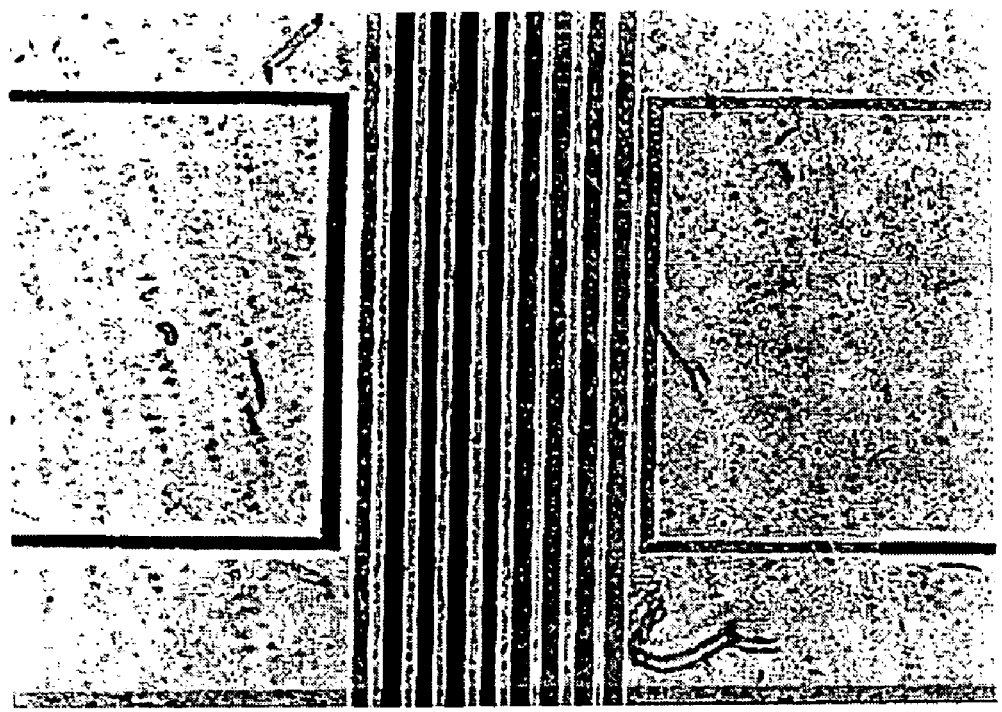
FIG. 7 shows an image of light transmission through a multi-channel silicone structure observed by a CMOS imager.
Figure 8A:
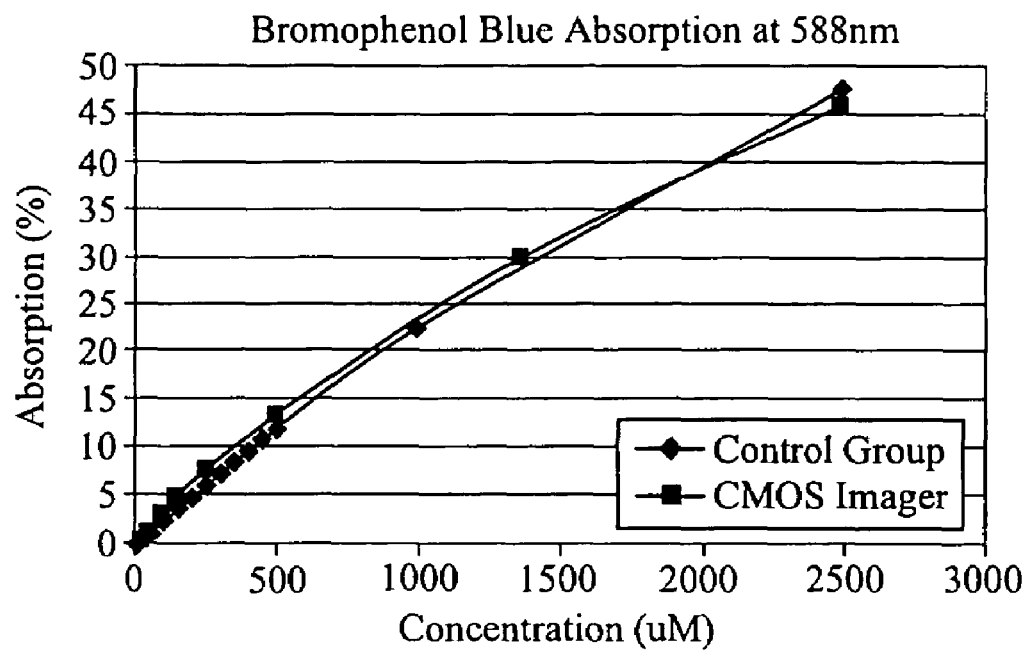
FIG. 8A shows measured absorption for bromophenol blue.
Figure 8B:
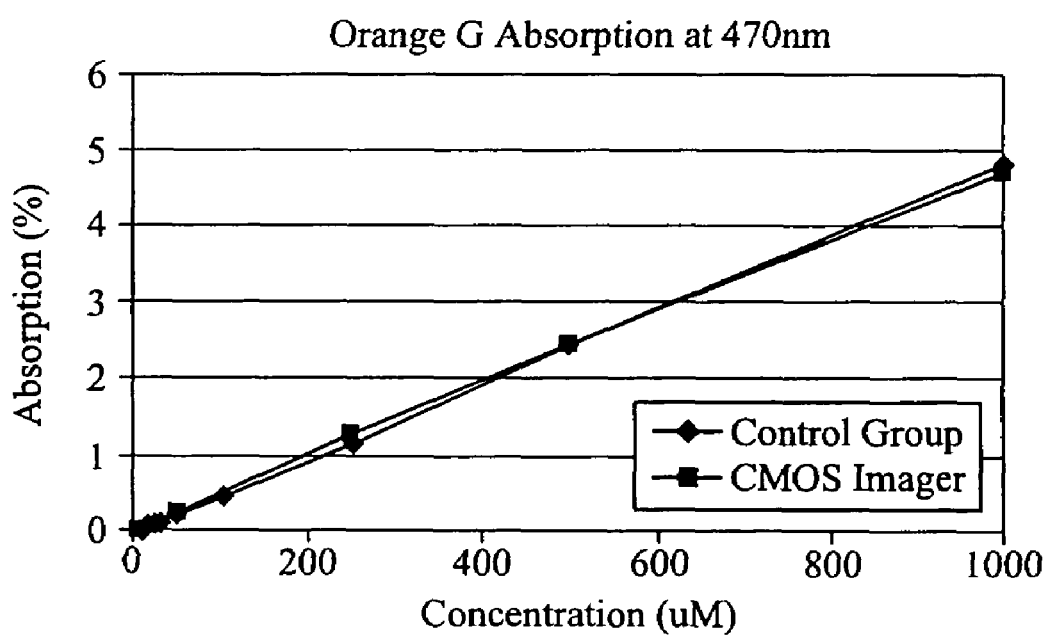
FIG. 8B shows measured absorption for Orange G.

Next, a polydimethylsiloxane ("PDMS") microfluidic chip having eleven 100 μm wide by 14 μm deep channels spaced 100 μm apart was placed on the CMOS imaging chip. The channels were filled with each concentration of interest and one channel was filled with water for background measurements. FIG. 7 shows an image of light transmission through the multi-channel silicone structure observed by the CMOS imager. The illumination source consisted of a Yellow AlInGaP LED with $\lambda_{max}$=588 nm and $I_0$=1500 mcd, and was optimized for the absorption peak of bromophenol blue. FIG. 7 is a black and white figure, so it may be difficult to distinguish the difference in the lower concentrations, but the imager can readily distinguish differences down to the sub-micromolar range. The results of the experiment are summarized in FIG. 8A. A similar test was conducted on Orange G, excited with light at 470 nm, as shown in FIG. 8B. Measurements were made by averaging the values from 5 μm long sections of the flow channel. Each of these sections has an approximate volume of 7 nl. The CMOS imager allows for individual sections to be analyzed, so any area which might have imperfections such as air or droplet formations could be selectively removed. From these figures, it is seen that the monolithic CMOS device displays similar performance to the commercial Shimadzu spectrometer system over the conditions tested.

Figure 9A:
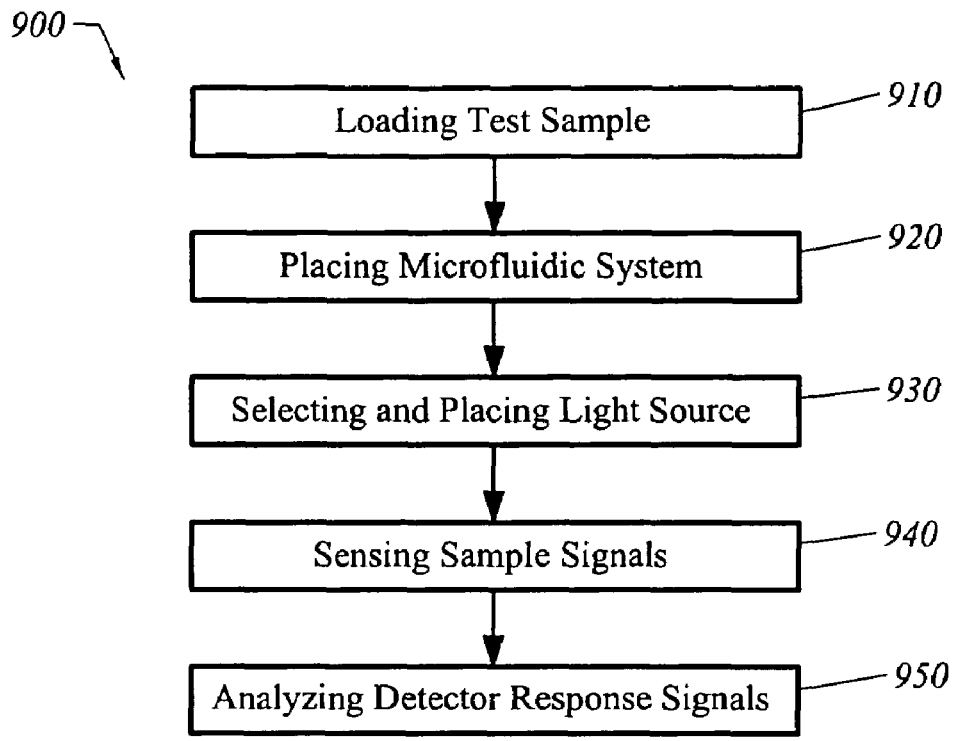
FIG. 9A is a simplified diagram for a method of using an integrated spectroscopic system for luminescence spectroscopy according to an embodiment of the present invention.

FIG. 9A is a simplified diagram for a method of using an integrated spectroscopic system for luminescence spectroscopy according to an embodiment of the present invention. For example, luminescence spectroscopy includes fluorescence spectroscopy and bio-luminescence spectroscopy. This diagram is merely an example, which should not unduly limit the scope of the claims. One of ordinary skill in the art would recognize many variations, alternatives, and modifications.

The method 900 of using an integrated spectroscopic system for luminescence spectroscopy includes process 910 of loading test samples into microfluidic system, processes 920 of placing the microfluidic system on top of a detector system or a bottom filter system, process 930 of selecting and placing a light source system, process 940 of sensing sample signals received at the detector system, process 950 of analyzing detector response signals, and possibly others, depending upon the embodiment.

Figure 9B:
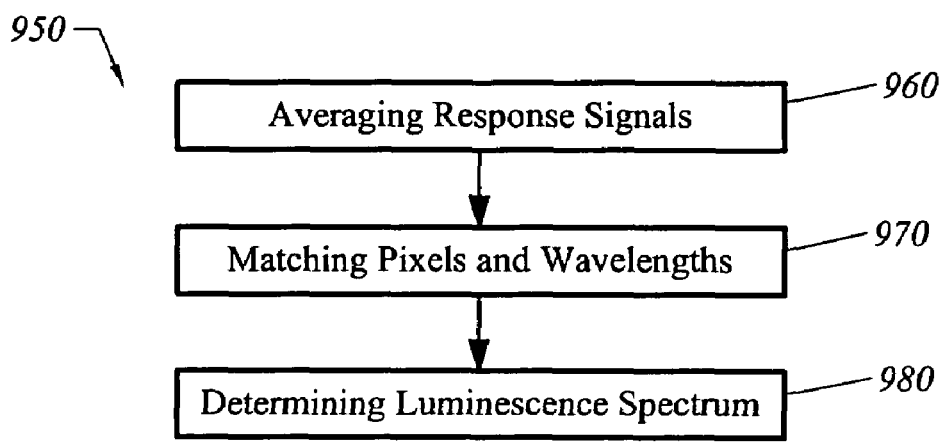
FIG. 9B is a simplified diagram for analyzing detector response signals according to an embodiment of the present invention.

Although the above has been shown using a selected sequence of processes, there can be many alternatives, modifications, and variations. For example, for fluorescence spectroscopy, at process 920, the microfluidic system is usually placed on top of the bottom filter system. Additionally, some of the processes may be expanded and/or combined. Process 930 of selecting and placing a light source system may include selecting and placing a top filter system. Process 950 of analyzing detector response signals may include process 960 of averaging response signals from pixels whose input sample signals have substantially the same wavelength, process 970 of matching individual pixels and wavelengths of their input sample signals, and process 980 of determining sample luminescence spectrum, as shown in FIG. 9B. Depending upon the embodiment, the specific sequence of processes may be interchanged with others replaced. Processes 910 through 950 may be modified to acquire response signals resulting from a broadband of sample signals, without distinguishing sample's signal spectrum. For active luminescence spectroscopy, process 930 of selecting and placing a light source system may be skipped. Additionally, process processes 910 through 950 may be modified to acquire response signals resulting from a broadband of sample signals by removing bottom filter system. Further details of these processes are found throughout the present specification and more particularly below.

Figure 10:
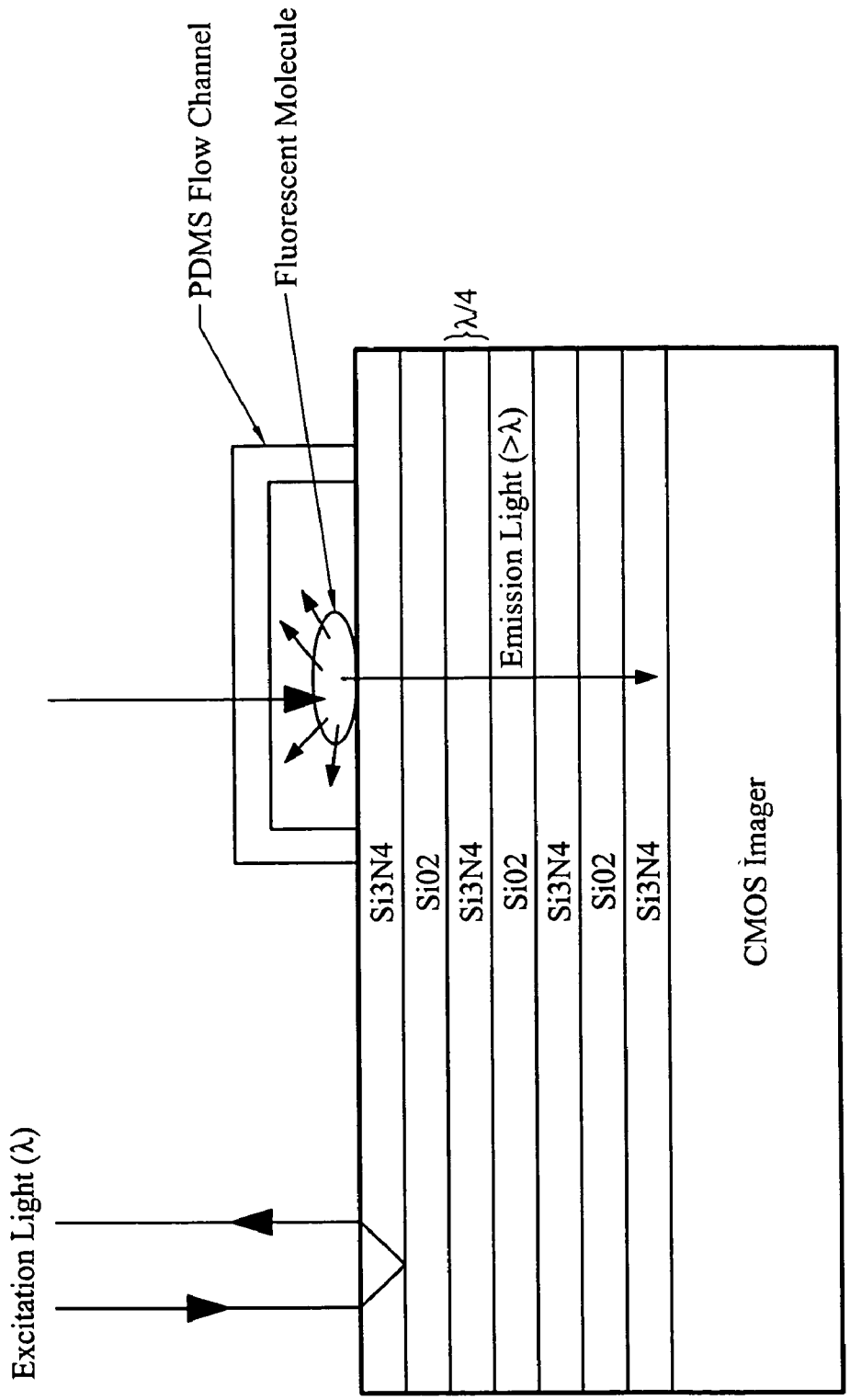
FIG. 10 is a simplified diagram for measuring fluorescence spectrum with a blocking filter.

During fluorescence spectroscopy, the sample under test is usually excited with a light source whose wavelength is close, for example within 40-80 nm, to the emitted fluorescent light. Usually, the light pump source is much brighter than the fluorescence signal, especially for experiments involving small numbers of fluorescing dye molecules, such as when performing single cell detection. Without an efficient filter, the pump beam saturates the imager, reducing chance of identifying the fluorescent signal. A blocking filter tuned to the pump wavelength can be placed between the microfluidic device and the imager, and should be substantially transparent at the fluorescent wavelength. The filter can easily be fabricated as a carefully grown dielectric thin-film mirror, as shown in FIG. 10. Such a filter, deposited by reactive sputter deposition of alternate ¼ layers of silicon dioxide and silicon nitride, is transparent at the fluorescent wavelength, and blocks over 99% of the incident pump wavelength.

EXAMPLE OF FLUORESCENCE EXPERIMENT

For example, an experiment measuring fluorescence spectroscopy was performed on diluted fluorescein dye. In FIG. 10, the bottom filter system and the microscopic system are deposited on the silicon CMOS detector array, so the contact image from this array can be used to differentiate between concentrations of fluorescein. The bottom filter system includes a blocking mirror having multiple dielectric layers. These dielectric layers are made of either silicon oxide or silicon nitride. The thickness of each dielectric layer equals to one quarter of the blocked wavelength in the respective layer. This diagram is merely an example, which should not unduly limit the scope of the claims. One of ordinary skill in the art would recognize many variations, alternatives, and modifications.

Figure 11A:
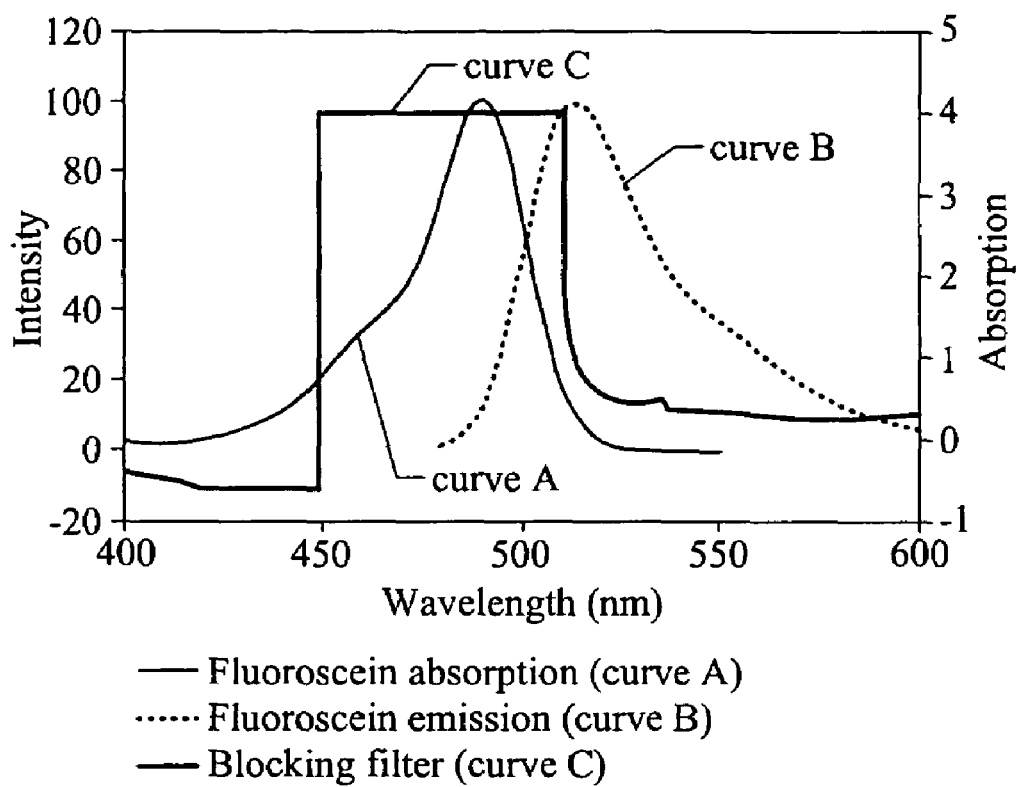
FIG. 11A shows a simplified effect of a blocking filter.

For example, spectrally resolved fluorescence measurements can be accomplished by slowly varying the spectral position of the reflectivity edge of the dielectric blocking mirror and measuring fluorescence intensities in different sensor pixels protected with filters with different reflectivity edges. Change of spectral position may be accomplished by varying thickness of each dielectric layer at different spatial locations or by rotating the blocking mirror along an axis parallel to the top surface of the detector system. In sum, the requirement for obtaining a high-quality fluorescence image on a miniaturized chip-based spectrometer usually relies on efficient blocking of the incident excitation light by the bottom filter system whose absorption spectrum is shown in FIG. 11A.

Figure 11B:
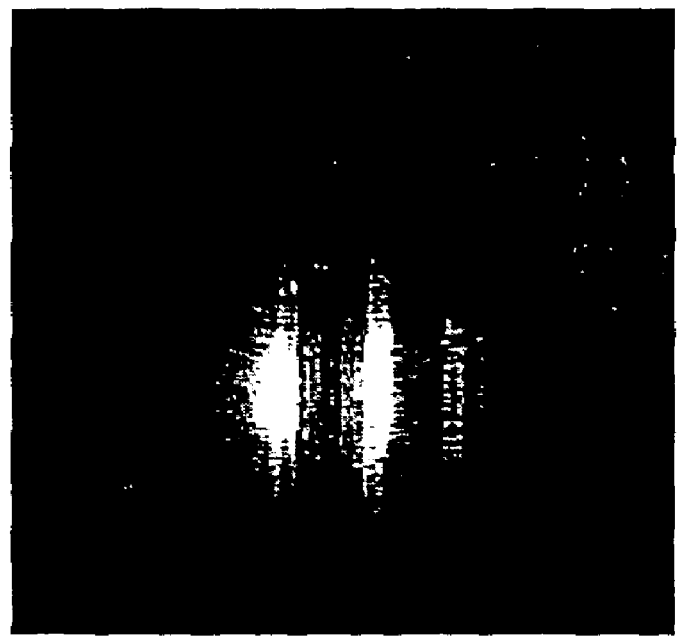
FIG. 11B depicts an acquired fluorescence sample image.
Figure 11C:
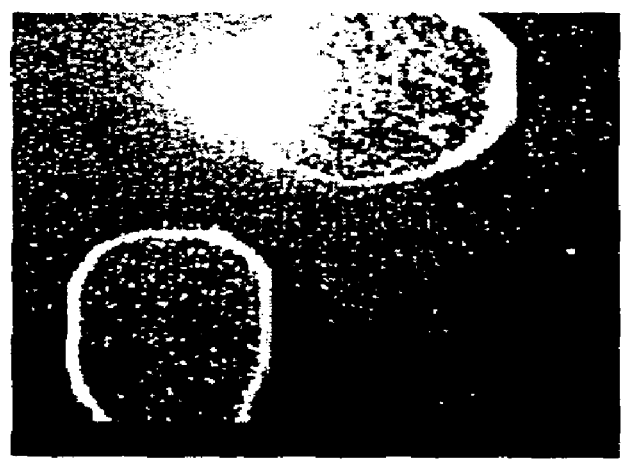
FIG. 11C shows an acquired image of fluorescent and non-fluorescent latex beads.

FIG. 11B depicts a sample image acquired with the experiment as shown in FIG. 10. In FIG. 11B, two channels were filled with different concentrations of fluorescein and illuminated with laser light. The channels were 100 μm wide and spaced 100 μm apart. The channel that resides in between the two test channels was filled with water for reference purposes. FIG. 11B illustrates that virtually all of the excitation light was blocked, and only fluorescence light was acquired by the imager. As stated previously, the reader may find it difficult to distinguish a difference between the two channels due to the loss of resolution in conversion of the imager data to picture format; however, the imager is capable of making the distinction. In yet another example, FIG. 11C shows CMOS images of both 5 micron fluorescent and non-fluorescent latex beads under the excitation of 488 nm Ar ion laser. In this example, a blocking filter system was also used on the imager.

Certain embodiments of the present invention has numerous advantages. For example, the imager spectrometer of the present invention can characterize spectra from picoliter volumes and observe a large number of flow channels simultaneously. Additionally, the present invention uses inexpensive and disposable fluidic components, and a very compact, robust and monolithic optical excitation and measurement system. The optical read-out system can remain reusable for many experiments and can sensitively detect diagnostic imaging information on the condition of flow channels. With the appropriate information processing, such an integrated system of the present invention can yield rapid, accurate results in a very short time. This coupled with the flexibility of soft lithography shows potential promises of a spectroscopic laboratory on a chip in which either absorption or luminescence can be measured and intelligent analysis of microscopic fluid volumes can be undertaken.

Additionally, filtered detector arrays used in some embodiments of the present invention can miniaturize spectroscopic instruments in microfluidic applications and provide "lensless" images of contents in flow channels. Moreover, imager elements based on CMOS technology used in some embodiments of the present invention offer compatibility with other CMOS processes such as VLSI for integrating onboard signal processing. Potential applications of the present invention includes outdoor testing of water quality, fast DNA fluorescence analysis at hospitals, and many others.

Moreover, the present invention can be used with elastomer-based microfluidic system. One advantage of using elastomeric flow channels is the inherent transparency of the elastomer material in the visible wavelength range and similar UV absorption characteristics to those of glass. This property enables the easy integration of elastomer microfluidic devices with standard optoelectronic sources and detectors. Moreover, silicone elastomers are simple to integrate on top of already fully fabricated detector arrays, forming a hermetic seal to the passivation layer of the detector arrays.

It is understood the examples and embodiments described herein are for illustrative purposes only and that various modifications or changes in light thereof will be suggested to persons skilled in the art and are to be included within the spirit and purview of this application and scope of the appended claims.

What is claimed is:

1. An apparatus for optical analysis, the apparatus comprising:
   a detector system;
   a microfluidic system on the detector system, the microfluidic system including a sealing membrane, the sealing membrane forming a surface of the microfluidic system;
   a light source system coupled to the microfluidic system;
   wherein the apparatus is free from any lens system between the microfluidic system and the detector system.

2. The apparatus of claim 1, wherein the microfluidic system is made of at least one selected from a group consisting of quartz, glass, and semiconductor.

3. The apparatus of claim 1, wherein the microfluidic system comprises one or a plurality of flow channels.

4. An apparatus for optical analysis, the apparatus comprising:
   a detector system;
   a microfluidic system on the detector system;
   wherein:
      the apparatus is free from any lens system between the microfluidic system and the detector system;
      the microfluidic system further comprises at least a sealing membrane, the sealing membrane forming a bottom surface of the microfluidic system.

5. The apparatus of claim 4, wherein the microfluidic system are made of elastomer.

6. The apparatus of claim 5, wherein the microfluidic system are made of PDMS.

7. The apparatus of claim 1 further wherein the light source system is separate from the detector system.

8. The apparatus of claim 7 wherein the light source system comprises at least one selected from a group consisting of a tungsten filament lamp, a tungsten-iodine filament lamp, a light emitting diode, a laser light source, and the Sun.

9. The apparatus of claim 1, wherein the detector system receives illumination transmitting through the microfluidic system in at least a portion of visible spectral range.

10. The apparatus of claim 9, wherein the detector system receives illumination transmitting through the microfluidic system in at least a portion of ultraviolet range.

11. The apparatus of claim 10, wherein the microfluidic system comprises at least one fluid channel, the fluid channel having a characteristic depth of about 10 microns.

12. The apparatus of claim 11, wherein the detector system comprises an imaging surface, the imaging surface having a characteristic area of about one square centimeter.

13. The apparatus of claim 11, wherein the microfluidic system on the detector system comprises:
   at least one sealing membrane, the sealing membrane being positioned at a bottom of the microfluidic system;
   at least one flow channel on the at least one sealing membrane.

* * * * *